US011530455B2

(12) United States Patent
Zhong

(10) Patent No.: US 11,530,455 B2
(45) Date of Patent: Dec. 20, 2022

(54) PENTA E POLYMORPHISMS FOR HUMAN IDENTIFICATION

(71) Applicant: LIFE TECHNOLOGIES CORPORATION, Carlsbad, CA (US)

(72) Inventor: Chang Zhong, Stanford, CA (US)

( * ) Notice: Subject to any disclaimer, the term of this patent is extended or adjusted under 35 U.S.C. 154(b) by 5 days.

(21) Appl. No.: 17/099,621

(22) Filed: Nov. 16, 2020

(65) Prior Publication Data

US 2021/0130913 A1    May 6, 2021

Related U.S. Application Data

(62) Division of application No. 15/155,440, filed on May 16, 2016, now Pat. No. 10,844,441.

(51) Int. Cl.
*C12Q 1/6888* (2018.01)
*C12Q 1/6881* (2018.01)
*C12Q 1/6858* (2018.01)

(52) U.S. Cl.
CPC ......... *C12Q 1/6888* (2013.01); *C12Q 1/6858* (2013.01); *C12Q 1/6881* (2013.01); *C12Q 2600/156* (2013.01)

(58) Field of Classification Search
None
See application file for complete search history.

(56) References Cited

U.S. PATENT DOCUMENTS

| 9,752,187 B2 * | 9/2017 | Wasserstrom ....... C12Q 1/6809 |
| 2009/0123928 A1 | 5/2009 | Wood et al. |
| 2012/0003634 A1 | 1/2012 | Frumkin et al. |
| 2012/0122093 A1 | 5/2012 | Hennessy et al. |
| 2016/0275240 A1 | 9/2016 | Huelga et al. |

FOREIGN PATENT DOCUMENTS

| AU | 2015246066 A1 * | 5/2017 |
| CN | 102286477 | 12/2011 |
| EP | 0487218 | 5/1992 |
| EP | 0512334 | 11/1992 |
| WO | 90/10064 | 9/1990 |
| WO | 91/03573 | 3/1991 |
| WO | 2011/070441 | 6/2011 |
| WO | 2017/201070 | 11/2017 |

OTHER PUBLICATIONS

ABI PRISM 310 Genetic Analyzer, pp. 1-4 [Product catalog, retrieved on-line, retrieved on Jan. 15, 2020, retrieved from: http://tools.thermofisher.com/content/sfs/brochures/cms_040736.pdf], (Year: 2004).

Buel et al., "Capillary Electrophoresis STR Analysis: Comparison to Gel-Based Systems", Journal of Forensic Sciences, vol. 43, No. 1, Jan. 1998, 164-170.

De Bellis et al., "Ligase detection reaction (LDR) and universal array (Zip Code): application to DNA genotyping", Minerva Biotecnologica, vol. 14, No. 3-4, 2002, 247-252.

Gen Bank Accession No. AJ580310 [publicly available October, retrieved on-line, retrieved on Jan. 15, 2020, retrieved from: https://www.ncbi.nlm.nih.gov/nucleotide/AJ580310.1?report=genbank&log$=nuclalign&blast_rank=2&RID=1YCBBR5G01R], (Year:2008).

Gerry et al., "Universal DNA Microarray Method for Multiplex Detection of Low Abundance Point Mutations", Journal of Molecular Biology, vol. 292, No. 2, Sep. 17, 1999, 251-262.

Higuchi et al., "Kinetic PCR Analysis: Real-Time Monitoring of DNA Amplification Reactions", BioTechnology, vol. 11, No. 9, Sep. 1993, 1026-1030.

Higuchi et al., "Simultaneous Amplification and Detection of Specific DNA Sequences", BioTechnology, vol. 10, No. 4, Apr. 1992, 413-417.

Hyungwoong et al., "Detection of very large off-ladder alleles at the PentaE locus in a 15 locus automomal STR database of 199 Korean individuals" Forensic Science International: Genetics, vol. 6, No. 6, Jun. 2012, e189-191.

International Preliminary Report on Patentability received for PCT Patent Application No. PCT/US17/32939, dated Nov. 29, 2018, 7 pages.

Krenke et al., "Validation of a 16-Locus Fluorescent Multiplex System," J. Forensic Sci., July, vol. 47, No. 4, pp. 1-13. (Year:2002).

Ng et al., "Multiplex PCR for the detection of tetracycline resistant genes," Molecular and Cellular Probes, vol. 15, pp. 209-215. ( Year: 2001).

PCT/US2017/032939,, "International Search Report and Written Opinion", dated Jul. 28, 2017, 1-12.

PowerPlex 16 Primer Pairs [NIST STRBase, retrieved on-line, retrieved on Jan. 14, 2020, retrieved from: https://strbase.nist.gov/PP16primers.html. (Year: 2020).

Stears, et al., "Trends in Microarray Analysis", Nature Medicine, vol. 9, No. 1, Jan. 2003, 140-145.

Thomson Scientific, "Database WPI Week 201228", 2012-A51731, London, GB, Dec. 21, 2011, 1-3.

Wenz et al., "High-Precision Genotyping by Denaturing Capillary Electrophoresis", Genome Research, vol. 8, Issue 1, Jan. 1998, 69-80.

\* cited by examiner

*Primary Examiner* — Young J Kim

(74) *Attorney, Agent, or Firm* — Workman Nydegger; Logan Christenson; John Guynn

(57) ABSTRACT

Methods for human identification using polymorphisms in the Penta E short tandem repeat locus are significant in preventing allelic drop out. An exemplary method encompasses (a) contacting a first primer to a nucleic acid sample to be analyzed, (b) contacting a second primer to the nucleic acid sample, and (c) subjecting the nucleic acid sample, the first primer, and the second primer to an amplification reaction, and thereby forming an amplification product. The first primer, the second primer, or both the first and second primers can be labeled with a non-nucleic-acid label. Additionally, or alternatively, the amplification product can include an adenosine at position 14 from the 5' end of SEQ ID NO:1, a thymidine at position 21 from the 5' end of SEQ ID NO:2, or both an adenine at position 14 and a thymidine at position 21 from the 5' end of SEQ ID NO:3.

20 Claims, 1 Drawing Sheet

Specification includes a Sequence Listing.

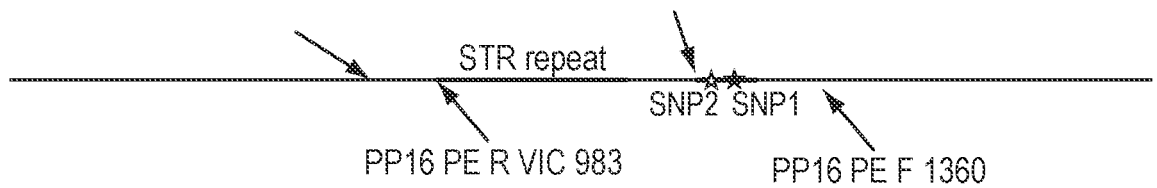

SEQUENCE LISTING

```
<160> NUMBER OF SEQ ID NOS: 9

<210> SEQ ID NO 1
<211> LENGTH: 22
<212> TYPE: DNA
<213> ORGANISM: Homo sapiens

<400> SEQUENCE: 1
aagaaaattg tggacaggtg cg                                              22

<210> SEQ ID NO 2
<211> LENGTH: 22
<212> TYPE: DNA
<213> ORGANISM: Homo sapiens

<400> SEQUENCE: 2
aagaaaattg tggccaggtg tg                                              22

<210> SEQ ID NO 3
<211> LENGTH: 22
<212> TYPE: DNA
<213> ORGANISM: Homo sapiens

<400> SEQUENCE: 3
aagaaaattg tggacaggtg tg                                              22

<210> SEQ ID NO 4
<211> LENGTH: 11
<212> TYPE: DNA
<213> ORGANISM: Homo sapiens

<400> SEQUENCE: 4
ggacaggtgc g                                                          11

<210> SEQ ID NO 5
<211> LENGTH: 11
<212> TYPE: DNA
<213> ORGANISM: Homo sapiens

<400> SEQUENCE: 5
```

```
<210> SEQ ID NO 6
<211> LENGTH: 11
<212> TYPE: DNA
<213> ORGANISM: Homo sapiens

<400> SEQUENCE: 6
ggacaggtgt g                                                              11

<210> SEQ ID NO 7
<211> LENGTH: 10
<212> TYPE: DNA
<213> ORGANISM: Homo sapiens

<400> SEQUENCE: 7
gacaggtgcg                                                                10

<210> SEQ ID NO 8
<211> LENGTH: 10
<212> TYPE: DNA
<213> ORGANISM: Homo sapiens

<400> SEQUENCE: 8
gccaggtgtg                                                                10

<210> SEQ ID NO 9
<211> LENGTH: 10
<212> TYPE: DNA
<213> ORGANISM: Homo sapiens

<400> SEQUENCE: 9
gacaggtgtg                                                                10
```

PENTA E POLYMORPHISMS FOR HUMAN IDENTIFICATION

RELATED APPLICATIONS

This application is a division of U.S. application Ser. No. 15/155,440 filed on May 16, 2019, now U.S. Pat. No. 10,844,441 which issued on Nov. 24, 2020—the contents of which are incorporated by reference in its entirety herein.

FIELD

Disclosed herein are methods and compositions for human identification using polymorphisms in the Penta E short tandem repeat locus.

INCORPORATION OF SEQUENCE LISTING

The instant application contains a Sequence Listing which has been submitted electronically in ASCII format and is hereby incorporated by reference in its entirety. Said ASCII copy, created on Nov. 6, 2020, is named LT01157DIV_SL.txt and is 1,607 bytes in size.

BACKGROUND

The fields of forensics, paternity testing, tissue typing, and personalized medicine routinely use DNA-based techniques for identity determinations, genotyping, phenotypic prediction, and in the prediction and/or prevention of disease. DNA typing involves the analysis of alleles of genomic DNA with characteristics of interest, commonly referred to as "markers." Most typing methods in use today are specifically designed to detect and analyze differences in the length and/or sequence of one or more regions of DNA markers known to appear in at least two different forms in a population. Such length and/or sequence variation is referred to as "polymorphism." Any region (i.e., "locus") of DNA in which such a variation occurs is referred to as a "polymorphic allele."

In recent years, the discovery and development of polymorphic short tandem repeats (STRs) as genetic markers has played an important role in DNA typing. STRs have become the primary means for human identity and forensic DNA testing. The Combined DNA Index System (CODIS) DNA database operated by the Federal Bureau of Investigation stores the DNA profile information of selected individuals. The profile includes 13 STR markers (13 loci with STR repeats), and AMEL, a sex determination locus. The selected DNA profiles are from convicted offenders, forensic, arrestee, missing or unidentified persons, and missing persons reference DNA (blood relative). Comparison of the DNA profile of an unidentified sample to CODIS DNA profiles has provided potential identification matches or investigative leads of possible perpetrators.

Matching DNA profiles produced from existing commercial STR assays with improved STR assays provides continuity and comparability of the DNA profiles within and between databases. An alteration in the DNA sequence due to, for example, a heretofore unknown mutation, polymorphism, or re-arrangement, can result in allelic dropout (the failure or significantly reduced amplification of a target nucleic acid). The occurrence of allelic dropout in new STR assays can make DNA profile matching within and between databases difficult or imprecise. Thus, design of new assays such that all potential amplification products within a population are detected remains an ongoing concern when developing STR assays. Therefore, there exists a need in the art, to improve DNA-based technologies based on the discovery of new variations in human DNA sequences.

SUMMARY OF SOME EMBODIMENTS OF THE INVENTION

In some embodiments, disclosed herein is a method for human identification encompassing hybridizing a first and second primer flanking the Penta E locus and amplifying the Penta E locus, wherein the amplifying yields at least an amplified product encompassing the sequence AAGAAAATTGTGGACAGGTGCG (SEQ ID NO:1), AAGAAAATTGTGGCCAGGTGTG (SEQ ID NO:2), or AAGAAAATTGTGGACAGGTGTG (SEQ ID NO:3).

In some embodiments, a method for human identification is disclosed encompassing hybridizing a first and second primer to the Penta E locus and amplifying the Penta E locus, wherein the amplifying yields at least two amplification products, one amplification product encompassing SEQ ID NO:1 and another amplification product encompassing SEQ ID NO:2. In other embodiments, the amplifying yields at least two amplification products, one amplification product encompassing SEQ ID NO:1 and another amplification product encompassing SEQ ID NO:3. In some embodiments, the amplifying yields at least two amplification products, one product encompassing SEQ ID NO:2 and another product encompassing SEQ ID NO:3.

In some embodiments, disclosed herein is a method encompassing selectively hybridizing at least a first and second primer flanking the Penta E locus, wherein the first primer is within 1,000 base pairs of the closest Penta E repeat and the first primer encompasses the sequence of GGACAGGTGCG (SEQ ID NO:4), GGCCAGGTGTG (SEQ ID NO:5), GGACAGGTGTG (SEQ ID NO:6), GACAGGTGCG (SEQ ID NO:7), GCCAGGTGTG (SEQ ID NO:8), GACAGGTGTG (SEQ ID NO:9), ACAGGTGCG, CCAGGTGTG, or ACAGGTGTG.

In some embodiments, disclosed herein is a method encompassing (a) contacting a first primer to a nucleic acid sample to be analyzed, (b) contacting a second primer to the nucleic acid sample, and (c) subjecting the nucleic acid sample, the first primer, and the second primer to an amplification reaction, and thereby forming an amplification product. In some embodiments, the first primer, the second primer, or both the first and second primers are labeled with a non-nucleic-acid label. The amplification product can include an adenosine at position 14 from the 5' end of SEQ ID NO:1, a thymidine at position 21 from the 5' end of SEQ ID NO:2, or both an adenine at position 14 and a thymidine at position 21 from the 5' end of SEQ ID NO:3.

In some embodiments, the method further includes separating the amplification product according to length and thereby forming a separated amplification product. The method can additionally include comparing the separated amplification product to an allelic ladder and thereby determining a Penta E repeat number associated with the nucleic acid sample. The separating can be, for example, by capillary gel electrophoresis. In some embodiments, the nucleic acid sample that is subjected to the amplification reaction is selected from the group comprising buccal cells, blood, blood on paper, buccal cells on paper, tissue, urine, saliva, vaginal cells, skin, and/or a fingerprint on paper.

BRIEF DESCRIPTION OF THE DRAWINGS

The skilled artisan will understand that the drawings described below are for illustration purposes only. The drawings are not intended to limit the scope of the present teachings in any way.

FIG. 1 illustrates the relative position of SEQ ID NOs:1, 2, and 3 (indicated as SNP2 and SNP1) to the Penta E short tandem repeat (indicated as "STR repeat"). The relative location of the instantly disclosed SEQ ID NOs: 1-3 to Promega PowerPlex 16 ("PP16") primers is also shown.

DESCRIPTION OF EXEMPLARY EMBODIMENTS

For the purposes of interpreting of this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). It is noted that, as used in this specification and the appended claims, the singular forms "a," "an," and "the," include plural referents unless expressly and unequivocally limited to one referent. The use of "or" means "and/or" unless stated otherwise. For illustration purposes, but not as a limitation, "X and/or Y" can mean "X" or "Y" or "X and Y".

The section headings used herein are for organizational purposes only and are not to be construed as limiting the described subject matter in any way. All literature cited in this specification, including but not limited to, patents, patent applications, articles, books, and treatises are expressly incorporated by reference in their entirety for any purpose. In the event that any of the incorporated literature contradicts any term defined herein, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The human genome is full of repetitive DNA sequences. Because these repeated DNA sequences can vary in number between individuals, these sequences are used in identifying individuals. The U.S. Federal Bureau of Investigation (FBI) launched an effort to establish a core set of loci for inclusion within a national database known as CODIS (Combined DNA Index System). The 13 CODIS loci are CSF1PO, FGA, TH01, TPOX, VWA, D3S1358, D5S818, D7S820, D8S1179, D13S317, D16S539, D18S51, and D21S11.

A "locus" is a specific position on a chromosome or a nucleic acid molecule. Alleles of a locus are located at identical sites on homologous chromosomes. Thus, the CODIS loci represent a collection of 13 specific positions on several different chromosomes. Owing to the repetitive nature of these loci, they are referred to as short tandem repeats. A "short tandem repeat (STR) locus" is a region of the human genome which contains short, repetitive sequence elements of 3 to 7 base pairs in length. The repeats at a given STR marker do not need to be perfect repeats. Examples of STRs, include but are not limited to, a triplet repeat; atcatcatc; a 4-peat; gatagata; and so on.

Identifying a human or identification of the human source of a biological sample(s) can be facilitated by determining the STR profile (that is, the alleles for a STR locus in the sample) for various loci (for example, CODIS loci), and comparing the results to an STR profile for the same various loci for a known sample or a database of STR profiles for known individuals. Comparing the STR profile of various loci in an unidentified sample with identified STR profiles can identify the human source of the biological sample, identify the human and/or provide investigative leads of possible perpetrators. Efficiency of obtaining the STR profile of an unknown sample can be facilitated by simultaneously analyzing a plurality of loci in a single reaction vessel.

After CODIS was established, scientists at Promega Corporation characterized the Penta E locus. The Penta E locus is a 5-peat (pentanucleotide) STR locus located on human Chromosome 15, with an AAAGA repeat motif. While the Penta E locus is not one of the CODIS loci, it is widely used for human identification purposes.

Disclosed herein is a polymorphic region closely linked with the Penta E locus. This polymorphic region is significant because failing to account for polymorphisms can render human identification assays, at best, inconclusive. A "polymorphism" or "DNA polymorphism" refers to the condition in which two or more different nucleotide sequences in a DNA sequence coexist in the same interbreeding population.

An example how the human identification assay can be rendered inclusive is allelic dropout. "Allelic dropout" refers to the failure or significantly reduced amplification of a target nucleic acid. Allelic dropout can result from failure of a primer's 3' terminus to bind to the primer binding site of a target nucleic acid. As a result there is no amplification of the target nucleic acid.

Primer

In some embodiments, disclosed herein is a method encompassing selectively hybridizing a first and second primer flanking the Penta E locus. The term "primer" refers to a polynucleotide (oligonucleotide) and analogs thereof that are capable of selectively hybridizing to a target nucleic acid or template.

A primer allows the synthesis of a sequence the reverse complement to the corresponding polynucleotide template, flanking sequence, or amplification product by extension from the primer's 3' end. Typically a primer can be between about 10 to 100 nucleotides in length and can provide a point of initiation for template-directed synthesis of a polynucleotide the reverse complement to the template, which can take place in the presence of appropriate enzyme(s), cofactors, and substrates such as nucleotides.

Primers can be mechanically synthesized. During cellular DNA replication short, newly produced DNA polynucleotides are formed. These naturally occurring DNA polynucleotides are called Okazaki fragments. Mechanically synthesized primers can differ from these naturally occurring Okazaki fragments by the absence of a 5' phosphate or by the presence of modifications, such as a label. These differences render mechanically synthesized primers chemically and functionally distinct from Okazaki fragments. For instance, the absence of a 5' phosphate would hinder the ligation of Okazaki fragments. And Okazaki fragments can contain ribonucleic acids (RNA).

In some embodiments, disclosed herein is a method encompassing selectively hybridizing a first and second primer flanking the Penta E locus, wherein the first primer does not possess a 5' phosphate. In other embodiments, disclosed herein is a method encompassing selectively hybridizing a first and second primer flanking the Penta E locus, wherein the second primer does not possess a 5' phosphate. In some embodiments, disclosed herein is a method encompassing selectively hybridizing a first and second primer flanking the Penta E locus, wherein the first and second primer do not possess a 5' phosphate. Thus, in some embodiments disclosed herein is a method encompassing selectively hybridizing a first and second primer flanking the Penta E locus and amplifying the Penta E locus, wherein the amplifying yields at least an amplified product encompassing the sequence SEQ ID NO:1, SEQ ID NO:2, or SEQ ID NO:3, and wherein the first primer does not possess a 5' phosphate, the second primer does not possess a 5' phosphate, or the first and second primer do not possess a 5' phosphate.

In some embodiments, disclosed herein is a method encompassing selectively hybridizing at least a first and second primer flanking the Penta E locus, wherein the first primer is within 1,000 base pairs of the closest Penta E repeat and possesses the sequence of SEQ ID NO:1, 2, 3, 4, 5, 6, 7, 8, 9, ACAGGTGCG, CCAGGTGTG, or ACAGGTGTG. In other embodiments, a method is disclosed encompassing selectively hybridizing at least a first, a second primer, and a third primer flanking the Penta E locus, wherein the first primer and second primer are within 1,000 base pairs of the closest Penta E repeat and wherein the first primer possesses the sequence of SEQ ID NO:1, 2, 3, 4, 5, 6, 7, 8, 9, ACAGGTGCG, CCAGGTGTG, or ACAGGTGTG and the second primer possesses the sequence of SEQ ID NO:1, 2, 3, 4, 5, 6, 7, 8, 9, ACAGGTGCG, CCAGGTGTG, or ACAGGTGTG wherein the first and second primers do not share the same SEQ ID NO. In some embodiments, the first, the second, and third primers do not possess a 5' phosphate. In other embodiments, the first and the second primers are labeled. In some embodiments, the first, the second, and the third primers are labeled.

In other embodiments, the first primer is labeled but the second and third primers are not. In some embodiments, the first and second primers are labeled but the third primer is not. In other embodiments, each of the primers is labeled with the same label. In some embodiments, the first and second primers are labeled with the same label.

The term "selectively hybridize" and variations thereof means that, under appropriate stringency conditions, a given sequence (for example, but not limited to, a primer) anneals with a second sequence comprising a reverse complementary string of nucleotides (for example, but not limited to, a target flanking sequence or a primer-binding site of an amplicon), but does not anneal to undesired sequences, such as non-target nucleic acids.

Typically, as the reaction temperature increases toward the melting temperature of a particular double-stranded sequence, the relative amount of selective hybridization generally increases. A statement that one sequence hybridizes or selectively hybridizes with another sequence encompasses embodiments where the entirety of both of the sequences hybridize to one another and embodiments where only a portion of one or both of the sequences hybridizes to the entire other sequence or to a portion of the other sequence.

As used herein, the term "stringency" refers to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required when it is desired that nucleic acids which are not completely complementary to one another be hybridized or annealed together. The art knows well that numerous equivalent conditions can be employed to comprise low stringency conditions.

Label

A "label" refers to moieties that be attached to nucleotides directly or indirectly to thereby render the molecule detectable by an instrument or method. For example, a label can be a moiety that: (i) provides a detectable signal or (ii) interacts with a second label to modify the detectable signal provided by the first or second label. Many different species of labels can be used, either individually or in combination with one or more different labels. A fluorophore is an example of a label.

"Fluorophore" refers to a moiety that is inherently fluorescent or demonstrates a change in fluorescence upon binding to a biological compound or metal ion, or when metabolized by an enzyme. Numerous fluorophores are known, examples of which include coumarins, acridines, furans, dansyls, cyanines, pyrenes, naphthalenes, benzofurans, quinolines, quinazolinones, indoles, benzazoles, borapolyazaindacenes, oxazines, and xanthenes, with the latter including fluoresceins, rhodamines, rosamines, and rhodols.

In some embodiments, the first and the second primers are labeled with a fluorophore. In some embodiments, the first, the second and third primers are labeled with a fluorophore.

In other embodiments, the first primer is labeled with a fluorophore but the second and third primers are not. In some embodiments, the first and second primers are labeled with a fluorophore but the third primer is not. In other embodiments, each of the primers is labeled with the same fluorophore. In some embodiments, the first and second primers are labeled with the same fluorophore.

Further examples of fluorophores include the following: 5- or 6-carboxyfluorescein (FAM™), VIC™ (a dye with a molecular weight of 550 and an absorbance maximum of 538 nm and an emission maximum of 554 nm), NED™, TAZ™, SID™, JOE™, TMR-ET, CXR-ET, BTG, BTY, BTR2, BTP, BTO, fluorescein, fluorescein isothiocyanate (FITC), IRD-700/800, cyanine dyes, such as CY3™, CY5™, CY3.5™, CY5.5™, Cy7™, xanthen, 6-carboxy-2', 4',7',4,7-hexachlorofluorescein (HEX™), 6-carboxy-l,4-dichloro-2',7'-dichloro-fluorescein (TET®), 6-carboxy-4',5'-dichloro-2',7'-dimethodyfluorescein (JOE™), N,N,N',N'-tetramethyl-6-carboxyrhodamine (TAMRA™), 6-carboxy-X-rhodamine (ROX™), 5-carboxyrhodamine-6G (R6G5), 6-carboxyrhodamine-6G (RG6), rhodamine, rhodamine green, rhodamine red, rhodamine 110, Rhodamin 6G®, BODIPY dyes, such as BODIPY TMR, oregon green, coumarines, such as umbelliferone, benzimides, such as Hoechst 33258; phenanthridines, such as Texas Red®, California Red®, Yakima Yellow, Alexa Fluor® 350, Alexa Fluor® 405, Alexa Fluor® 430, Alexa Fluor® 488, Alexa Fluor® 500, Alexa Fluor® 514, Alexa Fluor®532, Alexa Fluor® 546, Alexa Fluor® 555, Alexa Fluor® 568, Alexa Fluor® 594, Alexa Fluor® 610, Alexa Fluor® 633, Alexa Fluor® 647, Alexa Fluor® 660, Alexa Fluor® 680, Alexa Fluor® 700, Alexa Fluor® 750, PET®, ethidium bromide, acridinium dyes, carbazol dyes, phenoxazine dyes, porphyrine dyes, polymethin dyes, Atto 390, Atto 425, Atto 465, Atto 488, Atto 495, Atto 520, Atto 532, Atto 550, Atto 565, Atto 590, Atto 594, Atto 620, Atto 633, Atto 647N, Atto 655, Atto RhoG6, Atto Rhol I, Atto Rho2, Atto Rhol01, BMN™-5, BMN™-6, CEQ8000 D2, CEQ8000 D3, CEQ8000 D4, DY-480XL, DY-485XL, DY-495, DY-505, DY-510XL, DY-521XL, DY-521XL, DY-530, DY-547, DY-550, DY-555, DY-610, DY-615, DY-630, DY-631, DY-633, DY-635, DY-647, DY-651, DY-675, DY-676, DY-680, DY-681, DY-700, DY-701, DY-730, DY-731, DY-732, DY-750, DY-751, DY-776, DY-780, DY-781, DY-782, CAL Fluor® Gold 540, CAL Fluor RED 590, CAL Fluor Red 610, CAL Fluor Red 635, IRDye® 700Dx, IRDye® 800CW, Marina Blue®, Pacific Blue®, Yakima Yellow®, 6-(4,7-Dichloro-2',7'-diphenyl-3',6'-dipivaloylfluorescein-6-carboxamido)-hexyl-I-0-(2-cyanoethyl)-(N,N-diisopropyl)-phosphoramidite (SIMA), CAL Fluor® Gold 540, CAL Fluor® Orange 560, CAL Fluor Red 635, Quasar® 570, Quasar® 670, LIZ, Sunnyvale Red, LC Red® 610, LC Red® 640, LC Red®670, and LC Red®705.

Amplification

The present disclosure provides for a method, composition, and kit for amplifying the polymorphic region of the Penta E STR locus.

Nucleic acid amplification techniques are traditionally classified according to the temperature requirements of the amplification process. Isothermal amplifications are conducted at a constant temperature, in contrast to amplifications that require cycling between high and low temperatures. Examples of isothermal amplification techniques are: Strand Displacement Amplification, self-sustained sequence replication, the Qβ. replicase system, and the techniques disclosed in WO 90/10064 and WO 91/03573.

In some embodiments, disclosed herein is a method for human identification encompassing hybridizing a first and second primer flanking the Penta E locus and amplifying the Penta E locus, wherein the amplifying yields at least an amplified product encompassing the sequence SEQ ID NO:1, SEQ ID NO:2, or SEQ ID NO:3, and wherein the amplifying is an isothermal amplification process.

In some embodiments, a method for human identification is disclosed encompassing hybridizing a first and second primer to the Penta E locus and amplifying the Penta E locus, wherein the amplifying yields at least two amplification products, one amplification product encompassing SEQ ID NO:1 and another amplification product encompassing SEQ ID NO:2, and wherein the amplifying is an isothermal amplification process. In other embodiments, the amplifying yields at least two amplification products, one amplification product encompassing SEQ ID NO:1 and another amplification product encompassing SEQ ID NO:3, and wherein the amplifying is an isothermal amplification process. In some embodiments, the amplifying yields at least two amplification products, one product encompassing SEQ ID NO:2 and another product encompassing SEQ ID NO:3, and wherein the amplifying is an isothermal amplification process.

In some embodiments, disclosed herein is a method encompassing selectively hybridizing at least a first and second primer flanking the Penta E locus and amplifying the Penta E locus, wherein the first primer is within 1,000 base pairs of the closest Penta E repeat and encompasses the sequence of SEQ ID NO:4, SEQ ID NO:5, SEQ ID NO:6, SEQ ID NO:7, SEQ ID NO:8, SEQ ID NO:9, ACAGGTGCG, CCAGGTGTG, or ACAGGTGTG, and wherein the amplifying is an isothermal amplification process.

Examples of amplification techniques that require temperature cycling are: polymerase chain reaction (PCR), ligase chain reaction, ligase detection reaction (LDR), LDR-PCR, strand displacement amplification, transcription-based amplification, restriction amplification (U.S. Pat. No. 5,102,784), self-sustained sequence replication (or "3SR"), nucleic acid transcription-based amplification system, the Qβ replicase system and Rolling Circle Amplification, hybridization signal amplification, nucleic acid sequence-based amplification, the repair chain reaction, boomerang DNA amplification, and branched-DNA methods.

PCR employs a pair of amplification primers including an "upstream" or "forward" primer and a "downstream" or "reverse" primer, which delimit a region of the RNA or DNA to be amplified. A first primer and a second primer may be either a forward or reverse primer and are used interchangeably herein and are not to be limiting.

In some embodiments, disclosed herein is a method for human identification encompassing hybridizing a first and second primer flanking the Penta E locus and amplifying the Penta E locus, wherein the amplifying yields at least an amplified product encompassing the sequence SEQ ID NO:1, SEQ ID NO:2, or SEQ ID NO:3, and wherein the amplifying is an amplification process requiring thermal cycling. In some embodiments, the amplification process requiring thermal cycling is PCR.

In some embodiments, a method for human identification is disclosed encompassing hybridizing a first and second primer to the Penta E locus and amplifying the Penta E locus, wherein the amplifying yields at least two amplification products, one amplification product encompassing SEQ ID NO:1 and another amplification product encompassing SEQ ID NO:2, and wherein the amplifying is an amplification process requiring thermal cycling. In some embodiments, the amplification process requiring thermal cycling is PCR. In other embodiments, the amplifying yields at least two amplification products, one amplification product encompassing SEQ ID NO:1 and another amplification product encompassing SEQ ID NO:3, and wherein the amplifying is an amplification process requiring thermal cycling. In some embodiments, the amplification process requiring thermal cycling is PCR. In some embodiments, the amplifying yields at least two amplification products, one product encompassing SEQ ID NO:2 and another product encompassing SEQ ID NO:3, and wherein the amplifying is an amplification process requiring thermal cycling. In some embodiments, the amplification process requiring thermal cycling is PCR.

In some embodiments, disclosed herein is a method encompassing selectively hybridizing at least a first and second primer flanking the Penta E locus and amplifying the Penta E locus, wherein the first primer is within 1,000 base pairs of the closest Penta E repeat and encompasses the sequence of SEQ ID NO:4, SEQ ID NO:5, SEQ ID NO:6, SEQ ID NO:7, SEQ ID NO:8, SEQ ID NO:9, ACAGGTGCG, CCAGGTGTG, or ACAGGTGTG, and wherein the amplifying is an amplification process requiring thermal cycling. In some embodiments, the amplification process requiring thermal cycling is PCR.

Sample

"Sample" refers to a solid or liquid suspected of containing a nucleic acid. Examples of a sample include whole blood, plasma, serum, saliva, buccal cells, sweat, vaginal secretions, vaginal cells, semen, tissues, urine, or cerebrospinal fluid. A liquid culture medium used to grow cells can be a sample. The sample can be a filter paper upon which cells have been collected; for instance, buccal cells, blood cells, semen, or vaginal fluids. The sample can be a filter paper having been contacted to a surface, for instance a surface on which there is a fingerprint. The sample can be cloth upon which cells have been deposited. For instance, the sample can be cloth upon which blood, saliva, semen, or vaginal fluids have been applied. The sample can be a swab, or a portion thereof, upon which cells have collected; for instance, buccal cells, blood cells, semen, or vaginal fluids. The swab can be made of materials such as cotton or Nylon™. The sample can be a swab having been contacted to a surface; for instance, a surface on which there is a fingerprint, blood, saliva, or vaginal fluids. The sample can be an extract derived from a paper or a swab contacted to cells; that is, paper or swabs upon which nucleic acid extraction methods have been applied so as to collect released nucleic acids.

In some embodiments disclosed herein is a method encompassing contacting a first and a second primer to a sample, subjecting the sample to an amplification reaction and thereby forming a reaction product, wherein the reaction product encompasses SEQ ID NO:1, 2 or 3. In some embodiments the sample is blood. In other embodiments, the sample is blood applied to paper. In some embodiments, the sample is buccal cells. In other embodiments, the sample is buccal cells applied to paper. In some embodiments, the sample is paper swiped across a surface. In some embodiments, the surface possesses a fingerprint. In some embodiments, the first primer possesses the sequence of SEQ ID NO:1, 2, 3, 4, 5, 6, 7, 8, 9, ACAGGTGCG, CCAGGTGTG, or ACAGGTGTG. In other embodiments, the reaction product comprises an adenosine at position 14 from the 5' end of SEQ ID NO:1, a thymidine at position 21 from the 5' end of SEQ ID NO:2, or an adenine at position 14 and a thymidine at position 21 of SEQ ID NO:3. In some embodiments, the reaction product is labeled. In other embodiments, the label is a fluorophore. In some embodiments, the amplification reaction is a PCR.

The sample can be a mixed. That is, the sample can include solids or liquids or both suspected of containing a nucleic acid derived from more than one individual. For instance, a mixed sample can include vaginal secretions or vaginal cells and semen. Or for instance, a mixed sample can be cells from more than two persons. In some embodiments, the sample is a mixed sample.

The terms "amplicon," "amplification product" and "reaction product" are used interchangeably herein and refer to a broad range of techniques for increasing polynucleotide sequences, either linearly or exponentially and can be the product of an amplification reaction. An amplicon can be double-stranded or single-stranded and can include the separated component strands obtained by denaturing a double-stranded amplification product. In certain embodiments, the amplicon of one amplification cycle can serve as a template in a subsequent amplification cycle. Exemplary amplification techniques include, but are not limited to, PCR or any other method employing a primer extension step. Other nonlimiting examples of amplification include, but are not limited to, ligase detection reaction (LDR) and ligase chain reaction (LCR). Amplification methods can comprise thermal-cycling or can be performed isothermally. In various embodiments, the term "amplification product" includes products from any number of cycles of amplification reactions.

As used herein, the terms "identification" and "identity" are used interchangeably herein and refer to the identification of the individual and/or gender from which a sample or biological sample originated.

Polymerase

In some embodiments, disclosed herein is a composition encompassing a non-human polymerase, human genomic DNA, and an amplified product, wherein the amplified product encompasses SEQ ID NO:1, SEQ ID NO:2, or SEQ ID NO:3. In some embodiments, the amplified product is labeled. In other embodiments, the label is a fluorophore.

A "polymerase" is an enzyme that catalyzes the polymerization of a nucleotide. A DNA polymerase catalyzes the polymerization of deoxynucleotides.

A variety of bacterially derived nucleic acid polymerases can be used in the methods, compositions and kits described herein. For example, polymerases isolated from *Thermus aquaticus*, *Thermus thermophilus*, *Pyrococcus woesei*, *Pyrococcus furiosus*, *Thermococcus litoralis*, and *Thermotoga maritima*, *E. coli* DNA polymerase I, the Klenow fragment of *E. coli* DNA polymerase I, T4 DNA polymerase, T5 DNA polymerase, T7 DNA polymerase, and others.

In some embodiments disclosed herein is a composition encompassing a non-human polymerase, human genomic DNA, and an amplified product, wherein the amplified product encompasses SEQ ID NO:1, SEQ ID NO:2, or SEQ ID NO:3 and wherein the non-human polymerase is a bacterial DNA polymerase. In some embodiments, the bacterial DNA polymerase is a Taq polymerase or variant thereof.

The polymerase activity of any of the above enzymes can be determined by means known in the art. For example, polymerase activity can be measured as the rate of incorporation of $^{32}$P-dCTP into activated salmon sperm DNA. The reaction buffer can be, for example, 50 mM Tris-HCl (pH 8.0), 5 mM MgCl$_2$, 1 mM dithiothreitol (DTT), 50 µg/ml bovine serum albumin (BSA), and 4% (v/v) glycerol. Nucleotide substrates and DNA are used in large excess, typically at least 10 times the Km for the polymerase being assayed, e.g., 200 µM each of dATP, dTTP, and dGTP, 195 µM of dCTP plus 5 µM of labeled dCTP, and 250 µg/ml of activated DNA. The reactions are quenched on ice, and aliquots of the reaction mixture are spotted onto ion exchange filters. Unincorporated nucleotide is washed through, followed by scintillation counting to measure incorporated radioactivity.

"Genomic DNA" refers to the chromosomal DNA sequence of a gene or segment of a gene, including the DNA sequence of noncoding as well as coding regions. Genomic DNA also refers to DNA isolated directly from cells or chromosomes or the cloned copies of all or part of such DNA.

In some embodiments, a method of human identification is disclosed encompassing amplifying the Penta E locus from a genomic DNA, detecting the amplification product, an amplicon, wherein the amplicon contains the sequence of SEQ ID NO:1, 2 or 3, and the amplicon is indicative of the identity of a human. In some embodiments, the amplicon is labeled. In other embodiments, the label is a fluorophore.

Kit

As used herein, the term "kit" refers to any delivery system for delivering materials. In the context of reaction assays, such delivery systems include systems that allow for the storage, transport, or delivery of reaction reagents (e.g., oligonucleotides, enzymes, primer set(s), etc. in the appropriate containers) and/or supporting materials (e.g., buffers, written instructions for performing the assay, etc.) from one location to another. For example, kits can include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

In other embodiments, included are kits for human identification. In some embodiments, the kit comprises at least one pair of oligonucleotide primers for PCR amplification of Penta E locus wherein the first primer of the primer pair is within 1,000 base pairs of the closest Penta E repeat and the first primer encompasses the sequence of SEQ ID NO:4, SEQ ID NO:5, SEQ ID NO:6, SEQ ID NO:7, SEQ ID NO:8, SEQ ID NO:9, ACAGGTGCG, CCAGGTGTG, or ACAGGTGTG. In some embodiments, the kit further comprises an allelic ladder. The term "allelic ladder" as used herein refers to a standard size marker comprising a plurality of amplified alleles from a genetic marker. In some embodiments, the first primer is labeled. In other embodiments, the label is a fluorophore. In some embodiments, the second primer of the primer pair is labeled. In some embodiments, the second primer but not the first primer of the primer pair is labeled.

Analysis

Various methods can be used to analyze the products of the amplified alleles either by analyzing the individual amplified sequences or by analyses of a mixture of amplification products obtained from a multiplex reaction including. The term "allele" as used herein refers to a genetic variation associated with a gene or a segment of DNA, that is, one of two or more alternate forms of a DNA sequence occupying the same locus.

The terms "detecting" and "detection" are used in a broad sense herein and encompass any technique by which one can determine the presence of or identify a nucleic acid sequence. In some embodiments, detecting comprises quantitating a detectable signal from the nucleic acid, including without limitation, a real-time detection method, such as quantitative PCR ("Q-PCR"). In some embodiments, detecting comprises determining the sequence of a sequencing product or a family of sequencing products generated using an amplification product as the template; in some embodiments, such detecting comprises obtaining the sequence of a family of sequencing products.

Methods of detection include fluorescent labeled products, detection of radioisotope labeled products, silver staining of the amplification products, or the use of DNA intercalator dyes such as ethidium bromide (EtBr) and SYBR® Green cyanine dye to visualize double-stranded amplification products.

Fluorescent labels suitable for attachment to primers for use in the present teachings are numerous. With fluorescent analysis, at least one fluorescent labeled primer can be used for the amplification of each locus. Fluorescent detection may be desirable over radioactive methods of labeling and product detection, for example, because fluorescent detection does not require the use of radioactive materials, and thus avoids the regulatory and safety problems that accompany the use of radioactive materials. Fluorescent detection with labeled primers may also be selected over other non-radioactive methods of detection, such as silver staining and DNA intercalators, because fluorescent methods of detection generally reveal fewer amplification artifacts than do silver staining and DNA intercalators. This is due in part to the fact that only the amplified strands of DNA with labels attached thereto are detected in fluorescent detection, whereas both strands of every amplified product are stained and detected using the silver staining and intercalator methods of detection, which result in visualization of many non-specific amplification artifacts.

In some embodiments employed, fluorescent labeling of primers in a multiplex amplification reaction. As used herein, the term "multiplex" refers to at least two or more amplification reactions occurring simultaneously within a single amplification reaction vessel. Generally at least two different labels, at least three different labels, at least four different labels, at least five different labels, and at least six or more different labels can be used to label the two, three, four, five or at least six different primers. When a size marker is used to evaluate the products of the multiplex reaction, the primers used to prepare the size marker may be labeled with a different label from the primers that amplify the loci of interest in the reaction. With the advent of automated fluorescent imaging and analysis, faster detection and analysis of multiplex amplification products can be achieved.

In some embodiments of the present teaching, a fluorophore can be used to label at least one primer of the multiplex amplification, for example by being covalently bound to the primer, thus creating a fluorescent labeled primer. In some embodiments, primers for different target loci in a multiplex can be labeled with different fluorophores, each fluorophore producing a different colored product depending on the emission wavelength of the fluorophore. These variously labeled primers can be used in the same multiplex reaction, and their respective amplification products subsequently analyzed together. Either the forward or reverse primer of the pair that amplifies a specific locus can be labeled, although the forward can more often be labeled.

Various embodiments of the present teachings may comprise a single multiplex system comprising at least four different dyes. These at least four dyes may comprise any four of the above-listed dyes, or any other four dyes capable of producing signals that can be distinguished from one another, e.g., 6-FAM™, VIC®, NED™, and PET® dyes. Other embodiments of the present teaching may comprise a single multiplex system comprising at least five different dyes. These at least five dyes may comprise any five of the above-listed dyes, or any other five dyes capable of producing signals that can be distinguished from one another, e.g., 6-FAM™, VIC®, NED™, PET®, and LIZ® dyes. Other embodiments of the present teaching may comprise a single multiplex system comprising at least six different dyes. These at least six dyes may comprise any six of the above-listed dyes, or any other six dyes capable of producing signals that can be distinguished from one another, e.g., 6-FAM™, VIC®, NED™, PET®, LIZ® dyes, and a sixth dye (SID™) with maximum emission at approximately 620 nm. In some embodiments, TED dye or TAZ dye can be used in place of SID dye. The various embodiments of the subject method and compositions are not limited to any fixed number of dyes.

The PCR products can be analyzed on a sieving or non-sieving medium. In some embodiments of these teachings, for example, the PCR products can be analyzed by electrophoresis; for example, capillary electrophoresis, as described in H. Wenz et al. (1998), Genome Res. 8:69-80 (see also E. Buel et al. (1998), J. Forensic Sci. 43:(1), pp. 164-170)), or slab gel electrophoresis, as described in M. Christensen et al. (1999), Scand. J. Clin. Lab. Invest. 59(3): 167-177, or denaturing polyacrylamide gel electrophoresis (see, e.g., J. Sambrook et al. (1989), in Molecular Cloning: A Laboratory Manual, Second Edition, Cold Spring Harbor Laboratory Press, Cold Spring Harbor, N.Y., pp. 13.45-13.57). The separation of DNA fragments in electrophoresis is based primarily on differential fragment size. Amplification products can also be analyzed by chromatography; for example, by size exclusion chromatography (SEC).

In some embodiments, disclosed herein is a composition encompassing a labeled amplified product encompassing SEQ ID NO:1, SEQ ID NO:2, or SEQ ID NO:3 and a sieving or non-sieving medium. In other embodiments, a composition is disclosed encompassing labeled amplified product encompassing SEQ ID NO:1, SEQ ID NO:2, or SEQ ID NO:3, and a sieving or non-sieving medium and a size standard. In some embodiments, the medium is Performance Optimized Polymer (POP). In other embodiments, the medium is polymerized polyacrylamide. In other embodiments, the disclosed composition encompasses two or more labeled amplification products, wherein one labeled amplification product encompasses SEQ ID NO:1 and another labeled amplification product encompasses SEQ ID NO:2 and a sieving or non-sieving medium. In other embodiments, the composition further encompasses a size standard. In some embodiments, the medium is Performance Optimized Polymer (POP). In other embodiments, the medium is polymerized polyacrylamide. In other embodiments, the amplifying yields at least two labeled amplification products, one labeled amplification product encompasses SEQ ID NO:1 and another labeled amplification product encompasses SEQ ID NO:3 and a sieving or non-sieving medium. In other embodiments, the composition further encompasses a size standard. In some embodiments, the medium is Performance Optimized Polymer (POP). In other embodiments, the medium is polymerized polyacrylamide. In some embodiments, the amplifying yields at least two labeled amplification products, one labeled amplification product encompasses SEQ ID NO:2 and another labeled amplification product encompasses SEQ ID NO:3 and a sieving or non-sieving medium. In other embodiments, the composition further encompasses a size standard. In some embodiments, the medium is Performance Optimized Polymer (POP). In other embodiments, the medium is polymerized polyacrylamide.

Where fluorescent dyes are used to label amplification products, the electrophoresed and separated products can be analyzed using fluorescence detection equipment such as, for example, the ABI PRISM® 310 or 3130xl genetic analyzer, or an ABI PRISM® 377 DNA Sequencer (Applied Biosystems, Foster City, Calif.); or a Hitachi FMBIO™ II Fluorescent Scanner (Hitachi Software Engineering America, Ltd., South San Francisco, Calif.). In various embodiments of the present teachings, PCR products can be analyzed by a capillary gel electrophoresis protocol in conjunction with such electrophoresis instrumentation as the ABI PRISM3130xl genetic analyzer (Applied Biosystems), and allelic analysis of the electrophoresed amplification products can be performed, for example, with GeneMapper® ID Software v3.2, from Applied Biosystems. In other embodiments, the amplification products can be separated by electrophoresis in, for example, about a 4.5%, 29:1 acrylamide:bis acrylamide, 8 M urea gel as prepared for an ABI PRISM® 377 Automated Fluorescence DNA Sequencer.

In some embodiments, the detecting step can be combined with an amplifying step, for example, but not limited to, a melt curve determination. Exemplary means for performing a detecting step include the ABI PRISM® Genetic Analyzer instrument series, the ABI PRISM® Sequence Detection Systems instrument series, and the StepOne™ and Applied Biosystems Real-Time PCR instrument series (all from Applied Biosystems); and commercially available microarray and analysis systems available from Affymetrix, Agilent, and Amersham Biosciences, among others (see also Gerry et al., J. Mol. Biol. 292:251-62, 1999; De Bellis et al., Minerva Biotec. 14:247-52, 2002; and Stears et al., Nat. Med. 9:140-45, including supplements, 2003) or bead array platforms (Illumina, San Diego, Calif.). Exemplary software includes GeneMapper™ Software, GeneScan® Analysis Software, Genotyper® Software, and RapidFinder™ Software (all from Applied Biosystems).

In some embodiments the amplified allele is detected by monitoring the increase in the total amount of double-stranded DNA in the reaction mixture as described in Higuchi et al., 1992, BioTechnology 10:413-417; Higuchi et al., 1993, BioTechnology 11:1026-1030; and European Patent Publication Nos. 487,218 and 512,334, each incorporated herein by reference. The detection of double-stranded target DNA relies on the increased fluorescence that ethidium bromide (EtBr) and other DNA binding labels exhibit when bound to double-stranded DNA. The increase of double-stranded DNA resulting from the synthesis of target sequences results in a detectable increase in fluorescence.

While the principles of this invention have been described in connection with specific embodiments, it should be understood clearly that these descriptions are made only by way of example and are not intended to limit the scope of the invention. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence.

EXAMPLES

DNA Sample Preparation

An extensive population study was performed with a set of approximately 1500 anonymous Chinese ethnic (note the SNP was found only with Tibet sample) human samples, both from whole blood on paper substrate and buccal swabs. The blood on paper was directly PCR amplified. The buccal swabs were processed by Prep-n-Go lysis buffer, and followed with direct amplification of the lysate.

Amplification

A PCR reaction mix was prepared based on the following calculation per reaction:

| Component | Volume per reaction |
| --- | --- |
| Huaxia Platinum Master Mix (2.5X) | 10 μL |
| Huaxia Platinum Primer Set (2.5X) | 10 μL |
| Prep-n-Go lysis buffer | 5 μL |

Enough reagents for an additional 3 reactions were included in the calculation to provide excess volume for potential loss occurring during reagent transfers. The reagents were mixed by vortex at medium speed for 10 seconds followed by brief centrifugation to draw down any liquid which may have accumulated in the cap. 25 μL of the PCR reaction mix was placed into each reaction vial or well followed by the addition of a sample (a 1.2 mm disc). The tubes or wells were then covered and a brief centrifugation at 3000 rpm for about 30 seconds was performed to remove any air bubbles and to ensure that the disc was at the bottom of the vial or well prior to amplification.

PCR reactions were set up in MicroAmp™ 96-well reaction plates covered by either MicroAmp 8-cap strips or MicroAmp Clear Adhesive Film. The samples are amplified according to the following thermal cycling conditions: an initial incubation step at 95° C. for 1 min, 94° C. for 10 seconds denaturing, and 59° C. for 1.5 min; annealing for 30 cycles; and a final extension at 60° C. for 10 min. The resulting reactants can be held at 4° C. indefinitely. When using the GeneAmp PCR System 9700 with either 96-well silver or gold-plated silver block, select the Max Mode.

Cloning and Sequencing

The PCR Cloning and sequencing of the discordant alleles was performed by first PCR amplifying the blood disc samples with primers encompassing the Penta E repeat sequence. The PCR products were cloned using the TOPO™ TA cloning Kit for Sequencing (Thermo Fisher Scientific, Waltham, Mass.) and the bacterial transformation yielded numerous colonies. For each sample, 10 bacterial colonies were screened for the discordant alleles by diluting the colonies by $10^{-6}$-fold in water, PCR amplified for 25 cycles using the Penta E primers, and screening with the Applied Biosystems 3500xl Genetic Analyzer (Thermo Fisher Scientific, Waltham, Mass.). The colonies containing the discordant alleles and a number of selected control colonies containing the concordant alleles were picked for culturing overnight and the plasmid DNA of these colonies was purified with a QIAprep® Spin Miniprep Kit (Qiagen, Valencia, Calif.). Sequencing was performed using the BigDye Terminator v1.1 Cycle Sequencing Kit (Thermo Fisher Scientific) employing the M13 forward and reverse primers following the recommendations of the manufacturer. The sequencing reactions were carried out using approximately 200 ng of plasmid DNA and the unincorporated dye terminators were removed using the BigDye XTerminator™ Purification Kit (Thermo Fisher Scientific). Samples were electrophoresed on the Applied Biosystems 3130xl Genetic Analyzer using Performance Optimized Polymer (POP-4™ polymer) on a 36-cm capillary array. The sequences were analyzed using the DNA Sequencing Analysis software v5.2 (Thermo Fisher Scientific).

I claim:

1. A method comprising:
    contacting a first primer to a nucleic acid sample to be analyzed;
    contacting a second primer to the nucleic acid sample;
    subjecting the nucleic acid sample, the first primer, and the second primer to an amplification reaction, and thereby forming an amplification product,
        wherein the first primer, the second primer, or both the first and second primers are labeled with a non-nucleic-acid label,
        wherein the amplification product comprises an adenosine at position 14 from the 5' end of SEQ ID NO:1, a thymidine at position 21 from the 5' end of SEQ ID NO:2, or both an adenine at position 14 and a thymidine at position 21 from the 5' end of SEQ ID NO:3, and
        wherein the first primer encompasses a sequence selected from the group consisting of SEQ ID NO:4, SEQ ID NO:7, or ACAGGTGCG when the amplification product comprises SEQ ID NO:1; and
    analyzing the amplification product to identify a human.

2. The method of claim 1, further comprising separating the amplification product according to length, and thereby forming a separated amplification product.

3. The method of claim 2, further comprising comparing the separated amplification product to an allelic ladder and thereby determining a Penta E repeat number associated with the nucleic acid sample.

4. The method of claim 2, wherein the separating is by capillary gel electrophoresis.

5. The method of claim 1, wherein the non-nucleic-acid label is a fluorophore.

6. The method of claim 1, wherein the nucleic acid sample is selected from the group comprising buccal cells, blood, blood on paper, buccal cells on paper, tissue, urine, saliva, vaginal cells, skin, and a fingerprint on paper.

7. The method of claim 1, wherein the step of analyzing the amplification product to identify a human comprises making a paternity determination based on the amplification product.

8. The method of claim 1, wherein the nucleic acid sample to be analyzed is a forensic sample and wherein the step of analyzing the amplification product to identify a human comprises identifying a human associated with the forensic sample.

9. A method comprising:
    contacting a first primer to a nucleic acid sample to be analyzed;
    contacting a second primer to the nucleic acid sample; and
    subjecting the nucleic acid sample, the first primer, and the second primer to an amplification reaction, and thereby forming an amplification product,
        wherein the first primer, the second primer, or both the first and second primers are labeled with a non-nucleic-acid label,
        wherein the first primer and second primer are between 10 and 100 nucleotides in length, wherein the first primer encompasses a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, ACAGGTGCG, CCAGGTGTG, and ACAGGTGTG, and wherein the amplification product comprises an adenosine at position 14 from the 5' end of SEQ ID NO:1, a thymidine at position 21 from the 5' end of SEQ ID NO:2 or both an adenine at position 14 and a thymidine at position 21 from the 5' end of SEQ ID NO:3.

10. The method of claim 9, further comprising separating the amplification product according to length, and thereby forming a separated amplification product.

11. The method of claim 10, further comprising comparing the separated amplification product to an allelic ladder and thereby determining a Penta E repeat number associated with the nucleic acid sample.

12. The method of claim 10, wherein the separating is by capillary gel electrophoresis.

13. The method of claim 9, wherein the non-nucleic-acid label is a fluorophore.

14. The method of claim 9, wherein the nucleic acid sample is selected from the group comprising buccal cells, blood, blood on paper, buccal cells on paper, tissue, urine, saliva, vaginal cells, skin, and a fingerprint on paper.

15. The method of claim 9, wherein the step of analyzing the amplification product to identify a human comprises making a paternity determination based on the amplification product.

16. The method of claim 9, wherein the nucleic acid sample to be analyzed is a forensic sample and wherein the step of analyzing the amplification product to identify a human comprises identifying a human associated with the forensic sample.

17. A method for forming an amplification product, the method comprising:
providing a composition comprising a non-human polymerase, a human genomic DNA, and a label, wherein the label is a non-nucleic acid label; and
subjecting the composition to amplification conditions to form a non-nucleic acid labeled amplified product, wherein the non-nucleic acid labeled amplified product comprises SEQ ID NO:2 with a thymidine at position 21, or SEQ ID NO:3 with an adenine at position 14 and a thymidine at position 21.

18. A method for analyzing an amplification product, the method comprising:
providing a composition comprising a labeled amplified product and a capillary comprising a sieving medium or non-sieving medium, wherein the label is a non-nucleic acid label, and wherein the amplified product comprises SEQ ID NO:2 or SEQ ID NO:3; and
passing the labeled amplified product through the capillary.

19. The method of claim 18, wherein the composition further comprises a size standard, the method further comprising passing the size standard through the capillary.

20. The method of claim 18, wherein the sieving medium is a polymerized polyacrylamide.

* * * * *